(12) United States Patent
Seigneurin et al.

(10) Patent No.: US 8,343,520 B2
(45) Date of Patent: *Jan. 1, 2013

(54) COSMETIC COMPOSITION COMPRISING AN AMPHOLYTIC COPOLYMER

(75) Inventors: Aline Seigneurin, Le Chesnay (FR); Carole Foucault, Charenton le Pont (FR)

(73) Assignee: Rhodia Chimie, Cedex (FR)

( * ) Notice: Subject to any disclaimer, the term of this patent is extended or adjusted under 35 U.S.C. 154(b) by 2002 days.

This patent is subject to a terminal disclaimer.

(21) Appl. No.: 11/019,827

(22) Filed: Dec. 22, 2004

(65) Prior Publication Data

US 2005/0191265 A1 Sep. 1, 2005

(30) Foreign Application Priority Data

Dec. 23, 2003 (FR) ...................................... 03 15281

(51) Int. Cl.
*A61K 8/00* (2006.01)
*A61Q 19/10* (2006.01)
(52) U.S. Cl. ..................... 424/401; 424/70.1; 424/70.21; 424/70.12

(58) Field of Classification Search ........................ None
See application file for complete search history.

(56) References Cited

U.S. PATENT DOCUMENTS

| | | | | |
|---|---|---|---|---|
| 3,912,808 | A * | 10/1975 | Sokol | 424/70.2 |
| 4,333,921 | A * | 6/1982 | Luedicke et al. | 424/70.19 |
| 5,968,890 | A * | 10/1999 | Chambers et al. | 510/426 |
| 5,994,280 | A * | 11/1999 | Giret et al. | 510/130 |
| 6,569,261 | B1 | 5/2003 | Aubay et al. | 134/39 |
| 6,905,814 | B1 | 6/2005 | Aubay et al. | 430/947 |
| 2002/0052304 | A1 | 5/2002 | Aubay et al. | 510/361 |
| 2004/0013638 | A1 | 1/2004 | Aubay et al. | 424/78.37 |
| 2004/0234482 | A1* | 11/2004 | Muller et al. | 424/70.13 |

FOREIGN PATENT DOCUMENTS

| | | | |
|---|---|---|---|
| JP | 09-040532 A | * | 2/1997 |
| JP | 2003-277243 A | * | 10/2003 |
| WO | WO01/10213 | | 3/2001 |

* cited by examiner

*Primary Examiner* — Lakshmi Channavajjala
(74) *Attorney, Agent, or Firm* — Hunton & Williams, LLP

(57) ABSTRACT

The present invention relates to novel cosmetic compositions, more particularly for treating the skin or the hair, comprising an ampholytic artificial copolymer. The invention also relates to the use of the polymer in cosmetic compositions. The polymer comprises units derived from a polycationic monomer and units derived from a monomer of acidic nature.

24 Claims, No Drawings

COSMETIC COMPOSITION COMPRISING AN AMPHOLYTIC COPOLYMER

The present invention relates to novel cosmetic compositions, more particularly for treating the skin or the hair, comprising an ampholytic artificial copolymer. The invention also relates to the use of the polymer in cosmetic compositions.

It is sought, in compositions for treating the skin or the hair, intended to be applied and rinsed out, for instance shampoos or shower gels, to optimize certain properties, for instance the viscosity, the transparency, the deposition of material (conditioning effect) and/or, more generally, to optimize cosmetic effects such as the softness, the suppleness, the disentangling, the sheen or the styling capacity on dry or wet hair. Needless to say, besides the effects provided by the ingredients, formulations that are easy to prepare, easy to use and sufficiently stable are also sought.

It has thus been proposed to use in formulations intended to be rinsed out derivatives of natural polymers, for instance cationic derivatives of guar or of cellulose. Compositions have thus been proposed comprising combinations of cationic derivatives of guar and of polyorganosiloxanes, or combinations of cationic derivatives of cellulose and of polyorganosiloxane. These systems, like all systems, are a compromise between the amount of polymer used (which it is desired to be low), the transparency (which it is desired to be high, but which decreases when the amount of the polymer increases), and the conditioning properties associated with a deposit of the polyorganosiloxane (which it is desired to be high, and which can increase when the amount of polymer is increased). There is thus a need for novel compositions for which this compromise is modified.

It has also been proposed to use synthetic copolymers comprising cationic (or potentially cationic) units, anionic units and optionally neutral units. Thus, it has been proposed to use in certain formulations:
- copolymers derived from acrylic acid (AA, 2% to 40% by weight) and of dimethyldiallylammonium chloride (DADMAC, 60% to 90% by weight), for example in documents EP 269 243, EP 266 111 and EP 521 748, a commercial polymer being Merquat 280 sold by Calgon,
- copolymers derived from acrylic acid (AA, 35% by number), dimethyldiallylammonium chloride (DADMAC, 30% by number), and acrylamide (AM, 35% by number), for example in documents EP 522 755, EP 522 756 and EP 1 115 370, a commercial product being Merquat Plus 3330 sold by Calgon,
- copolymers derived from acrylic acid (AA), methacrylamidopropyltrimethylammonium chloride (MAPTAC) and alkyl acrylate, for example described in documents EP 522 756 and EP 1 115 370, a commercial polymer being Merquat 2001 sold by Calgon. (AA/MAPTAC/methyl acrylate).

It is still sought to propose novel cosmetic compositions, in particular intended to be rinsed out, which have improved qualities in terms of stability and/or simplification of the formulations and/or transparency and/or cosmetic qualities (mentioned above) and/or deposition of material (deposition of a polymer bearing cationic charges or deposition of other materials, for instance mineral oils, plant oils or synthetic oils, for example silicone oils, or "polyorganosiloxanes").

To this end, the invention proposes a cosmetic composition comprising a cosmetically acceptable vector, preferably water, optionally a surfactant and an ampholytic copolymer comprising cationic units (c) and anionic or potentially anionic units (a), characterized in that:

the polymer comprises:
0.1% to 50% by number of units (c) derived from the polymerization of at least one monomeric compound (c) of general formula I:

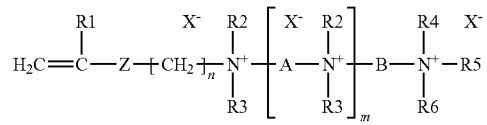

in which:
R$_1$ is a hydrogen atom or a methyl or ethyl group;
R$_2$, R$_3$, R$_4$, R$_5$ and R$_6$, which may be identical or different, are linear or branched C$_1$-C$_6$ and preferably C$_1$-C$_4$ alkyl, hydroxyalkyl or aminoalkyl groups,
m is an integer from 0 to 10 and preferably from 0 to 2;
n is an integer from 1 to 6 and preferably from 2 to 4;
Z represents a —C(O)O— or —C(O)NH— group or an oxygen atom;
A represents a group (CH$_2$)$_p$, p being an integer from 1 to 6 and preferably from 2 to 4;
B represents a linear or branched C$_2$-C$_{12}$ and advantageously C$_3$-C$_6$ polymethylene chain, optionally interrupted with one or more hetero atoms or hetero groups, especially O or NH, and optionally substituted with one or more hydroxyl or amino groups, preferably hydroxyl groups;
X$^-$, which may be identical or different, represent counterions;
units (a) derived from the polymerization of at least one hydrophilic monomer (a) bearing a function of acidic nature that is copolymerizable with (a), which is anionic or potentially anionic,
optionally units (n) derived from at least one ethylenically unsaturated monomer (n) of neutral charge, which is copolymerizable with (c) and (a), preferably an ethylenically unsaturated hydrophilic monomer compound of neutral charge bearing one or more hydrophilic groups, which is copolymerizable with (c) and (a),
the amount of units (a) and optionally (n) being from 50% to 99.9% by number,
the pH of the composition is greater than or equal to 5.5 and preferably between 5.5 and 7.5,
the weight proportion of surfactant in the composition is between 0 and 30% and preferably between 5% and 30% by weight, the surfactant comprising an anionic surfactant and optionally an amphoteric surfactant,
the weight proportion of the copolymer in the composition is between 0.01% and 5%, preferably between 0.05% and 1.5% and preferentially from 0.1% to 0.3%.

The compositions are preferably compositions intended to be rinsed out. Said composition may be, for example, a shampoo, a shower gel or a hair conditioner. However, it may be a haircare composition not intended to be rinsed out, for example a conditioner not intended to be rinsed out, a disentangling milk, a disentangling fluid, a smoothing fluid, a cuticle coating, a styling and/or restyling haircare product, an antisun product, a care cream, a makeup remover, a makeup, makeup-removing or moisturizing wipes, shaving foams or styling or fixing mousses.

The invention also relates to the use of the copolymer in cosmetic compositions.

Effects

The use of the polymer in the composition according to the invention may in particular afford an increase in viscosity. The polymer becomes deposited on the hair and/or the skin, and affords a desired conditioning effect. When the compositions comprise a conditioning agent, for example a silicone (also referred to as a polyorganosiloxane), they promote the deposition of said agent. The polymer thus aids the deposition of conditioning agents, more particularly silicones (or polyorganosiloxanes). In addition, the compositions comprising a polyorganosiloxane and the polymer have excellent conditioning properties, for the hair or the skin, and also advantageous sensory or cosmetic properties, which may be desired by consumers. Thus, they may afford an advantageous profile of softness, suppleness, volume, disentangling, styling capacity on wet hair and/or styling capacity on dry hair. These effects may make the formulations simpler and/or less expensive. The compositions also have satisfactory foaming properties, especially in hard water.

In particular, the copolymer according to the invention has great transparency. It may be used as a transparent agent. It especially makes it possible to prepare compositions of high transparency, with a high capacity for deposition (for example for conditioning) and/or a capacity for aiding the deposition of polyorgano-siloxanes (for example for conditioning), in particular during rinsing. The combination of small amounts of polymer, typically from 0.1% to 0.3% by weight of the composition, and even about 0.1%, with polyorgano-siloxanes affords compositions of high transparency, with a high level of deposition of the polyorgano-siloxane, and thus with an advantageous conditioning profile and/or an advantageous sensory or cosmetic profile.

Polymer

The copolymer comprises:
0.1% to 50% by number of units (c) derived from the polymerization of at least one monomer compound (c) of general formula I:

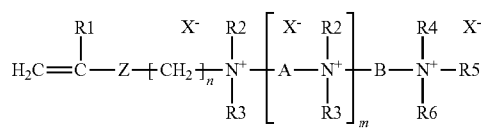

in which:
R$_1$ is a hydrogen atom or a methyl or ethyl group;
R$_2$, R$_3$, R$_4$, R$_5$ and R$_6$, which may be identical or different, are linear or branched C$_1$-C$_6$ and preferably C$_1$-C$_4$ alkyl, hydroxyalkyl or aminoalkyl groups,
m is an integer from 0 to 10 and preferably from 0 to 2;
n is an integer from 1 to 6 and preferably from 2 to 4;
Z represents a —C(O)O— or —C(O)NH— group or an oxygen atom;
A represents a group (CH$_2$)$_p$, p being an integer from 1 to 6 and preferably from 2 to 4;
B represents a linear or branched C$_2$-C$_{12}$ and advantageously C$_3$-C$_6$ polymethylene chain, optionally interrupted with one or more hetero atoms or hetero groups, especially O or NH, and optionally substituted with one or more hydroxyl or amino groups, preferably hydroxyl groups;
X$^-$, which may be identical or different, represent counterions;

units (a) derived from the polymerization of at least one hydrophilic monomer (a) bearing a function of acidic nature that is copolymerizable with (a), which is anionic or potentially anionic, optionally units (n) derived from at least one ethylenically unsaturated monomer (n) of neutral charge, which is copolymerizable with (c) and (a), preferably an ethylenically unsaturated hydrophilic monomer compound of neutral charge bearing one or more hydrophilic groups, which is copolymerizable with (c) and (a), the amount of units (a) and optionally (n) being from 50% to 99.9% by number.

The ion X$^-$ is advantageously chosen from halide, for example chloride, sulfate, methyl sulfate, hydrosulfate, phosphate, citrate, formate and acetate.

The monomer (c) may be prepared, for example, according to the following reaction schemes:

- reaction scheme 1:
(when m is equal to 0)

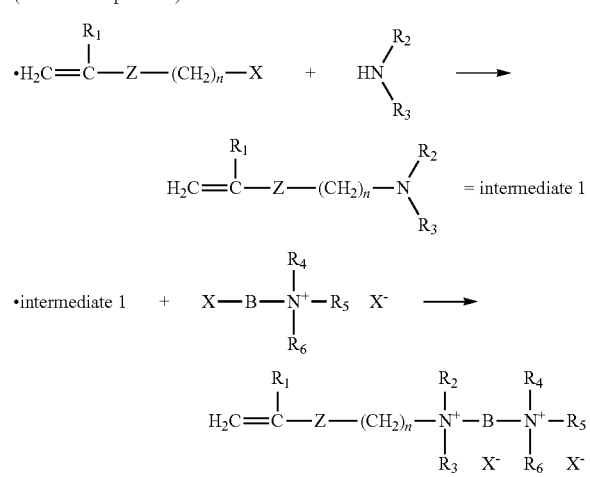

reaction scheme 2:
(when m is equal to 1)

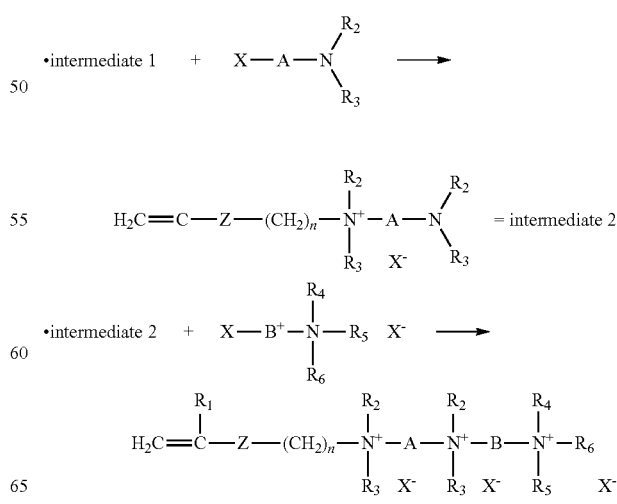

reaction scheme 3:
(when m is between 2 and 10)

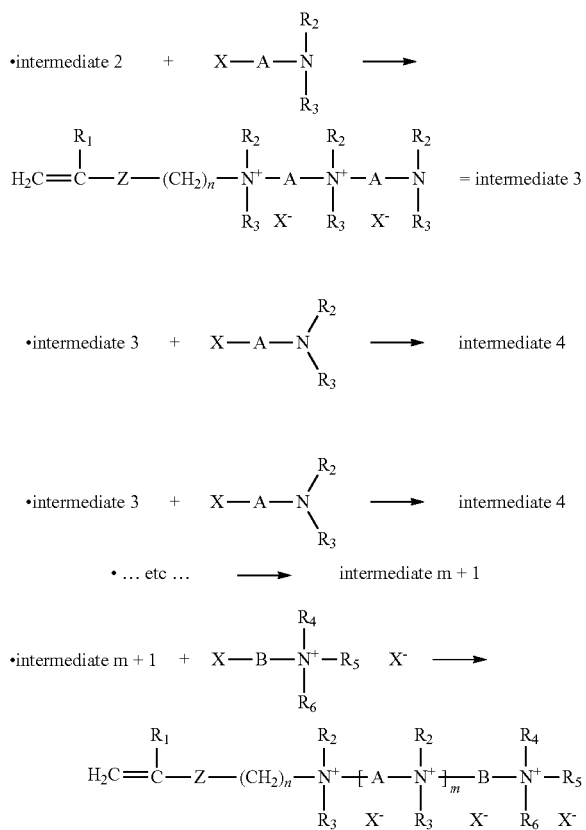

The copolymer according to the invention advantageously has a molecular mass of at least 1000 and advantageously of at least 10 000; it may be up to 20 000 000 and advantageously up to 10 000 000. It is preferably between 500 000 and 5 000 000.

Unless otherwise mentioned, when the term molecular mass is used, it will be the weight-average molecular mass, expressed in g/mol. This may be determined by aqueous gel permeation chromatography (GPC) or by measurement of the intrinsic viscosity in a 1N solution of $NaNO_3$ at 30° C.

The copolymer is preferably a random copolymer. Preferably, in the general formula (I) of the monomer (c), Z represents C(O)O, C(O)NH or O, and most preferably C(O)NH;

n is equal to 2 or 3 and most particularly 3 m ranges from 0 to 2, it is preferably equal to 0 or 1 and most particularly 0;

B represents:

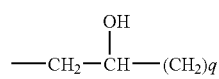

with q from 1 to 4, preferably equal to 1;

$R_1$ to $R_6$, which may be identical or different, represent a methyl or ethyl group.

The preferred monomer (c) is the DIQUAT having the following formula:

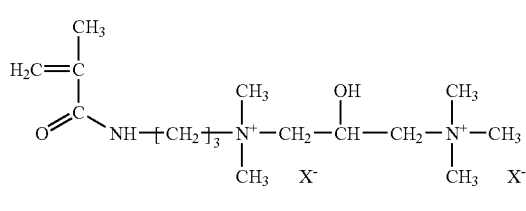

$X^-$ representing a chloride or methyl sulfate ion.

Other monomers (c) that are particularly advantageous are:

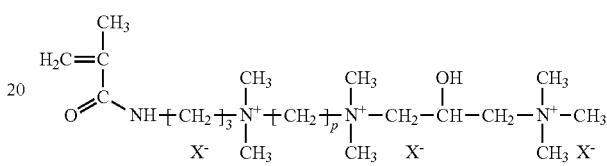

in which p=2 to 4.

The anions $X^-$ are especially a halogen anion, preferably a chloride, sulfonate, sulfate, methyl sulfate, hydrogen sulfate, phosphate, phosphonate, citrate, formate or acetate anion.

The monomers (a) are advantageously monoethylenically unsaturated $C_3$-$C_8$ carboxylic, sulfonic, sulfuric, phosphonic or phosphoric acids, anhydrides thereof and water-soluble salts thereof.

Among the preferred monomers (a) that may be mentioned are acrylic acid, methacrylic acid, α-ethacrylic acid, β,β-dimethylacrylic acid, methylenemalonic acid, vinylacetic acid, allylacetic acid, ethylidineacetic acid, propylidineacetic acid, crotonic acid, maleic acid, fumaric acid, itaconic acid, citraconic acid, mesaconic acid, N-methacryloylalanine, N-acryloylhydroxyglycine, sulfo-propyl acrylate, sulfoethyl acrylate, sulfoethyl methacrylate, sulfoethyl methacrylate, styrenesulfonic acid, vinylsulfonic acid, vinylphosphonic acid, phosphoethyl acrylate, phosphonoethyl acrylate, phosphopropyl acrylate, phosphonopropyl acrylate, phosphoethyl methacrylate, phosphonoethyl methacrylate, phosphopropyl methacrylate and phosphonopropyl methacrylate, and the alkali metal and ammonium salts thereof.

Among the monomers (n) that may be mentioned are acrylamide, vinyl alcohol, $C_1$-$C_4$ alkyl esters of acrylic acid and of methacrylic acid, $C_1$-$C_4$ hydroxyalkyl esters of acrylic acid and of methacrylic acid, especially ethylene glycol and propylene glycol acrylate and methacrylate, polyalkoxylated esters of acrylic acid and of methacrylic acid, especially the polyethylene glycol and polypropylene glycol esters, esters of acrylic acid or of methacrylic acid and of polyethylene glycol or polypropylene glycol mono($C_1$-$C_{25}$)alkyl ethers, vinyl acetate, vinylpyrrolidone and methyl vinyl ether.

The polymer comprises from 0.1% to 50% by number of units (c) and from 50% to 99.1% by number of units (a) and optionally (n). Preferably, the polymer comprises from 10% to 40% of units (c) and from 60% to 90% of units (a) and optionally (n). Moreover, the polymer advantageously does not comprise any units (n). If the polymer does comprise units (n), the molar ratio between the units (a) and the units (n) is preferably greater than 1, for example between 1 and 4.

Preferably, the polymer is such that
the units (c) are derived from a monomer (c) of the following formula:

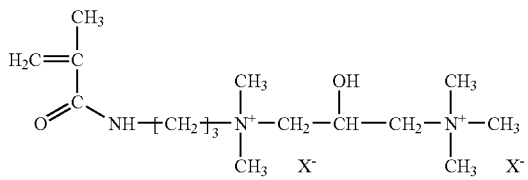

X⁻ representing a chloride or methyl sulfate ion,
the units (a) are derived from acrylic acid,
the polymer does not comprise any units (n),
the numerical ratio between the units (a) and the units (c) is from 50/50 to 90/10.

It is pointed out that the copolymers may have a mean negative or zero charge, at the pH of the composition or at the pH of use of the composition. This mean charge is defined by the following equation:

$$Q = \frac{[c]X_c - [a]X_a}{[c]X_c + [a]X_a}$$

in which:
[c] is the molar concentration of units (c),
[a] is the molar concentration of units (a),
$X_C$ represents the possible degree of neutralization of the units (a) $A_C$ (in the case where the units (a) are potentially cationic); $X_c=[BH^+]/([B]+[BH^+])$,
$X_A$ represents the possible degree of neutralization of the units (c) (in the case where the units (c) are potentially anionic); $X_A=[A^-]/([AH]+[A^-])$.

The copolymers of the invention may be obtained according to the known techniques for the preparation of copolymers, especially by free-radical polymerization of ethylenically unsaturated starting monomers that are known compounds or that may be readily obtained by a person skilled in the art using standard synthetic processes of organic chemistry.

Reference may be made especially to the processes described in U.S. Pat. No. 4,387,017 and EP 156 646.

The free-radical polymerization is preferably performed in an oxygen-free environment, for example in the presence of an inert gas (helium, argon, etc.) or nitrogen. The reaction is performed in an inert solvent, preferably methanol or ethanol, and more preferably in water.

The polymerization is initiated by adding a polymerization initiator. The initiators used are the free-radical initiators usually used in the art. Examples include organic peresters (t-butyl peroxy-pivalate, t-amyl peroxypivalate, t-butyl peroxy-α-ethylhexanoate, etc.); organic compounds of azo type, for example azobisamidinopropane hydrochloride, azobisisobutyronitrile, azobis-2,4-dimethylvaleronitrile, etc.); mineral and organic peroxides, for example hydrogen peroxide, benzyl peroxide and butyl peroxide, etc.; redox initiator systems, for example those comprising oxidizing agents, such as persulfates (especially ammonium or alkali metal persulfates, etc.); chlorates and bromates (including mineral or organic chlorates and/or bromates); reducing agents such as sulfites and bisulfites (including mineral and/or organic sulfites or bisulfites); oxalic acid and ascorbic acid, and also mixtures of two or more of these compounds.

The preferred initiators are water-soluble initiators. Sodium persulfate and azobisamidinopropane hydrochloride are particularly preferred.

As variant, the polymerization may be initiated by irradiation using ultraviolet light. The amount of initiators used is generally an amount that is sufficient to achieve initiation of the polymerization. The initiators are preferably present in an amount ranging from 0.001% to about 10% by weight relative to the total weight of the monomers, and are preferably included in an amount of less than 0.5% by weight relative to the total weight of the monomers, a preferred amount being in the range from 0.005% to 0.5% by weight relative to the total weight of the monomers. The initiator is added to the polymerization mixture either continuously or in a batchwise manner.

When it is desired to obtain copolymers of high molecular mass, it is desirable to add fresh initiator during the polymerization reaction. Gradual or batchwise addition also allows a more efficient polymerization and a shorter reaction time. The polymerization is performed under reaction conditions that are efficient for polymerizing the monomers (c), the monomers (a) and optionally the monomers (n) in an oxygen-free atmosphere. Preferably, the reaction is performed at a temperature ranging from about 30° to about 100° and preferably between 60° and 90° C. The oxygen-free atmosphere is maintained throughout the reaction, for example by maintaining a flow of nitrogen throughout the reaction.

One copolymer that is particularly preferred is the following:

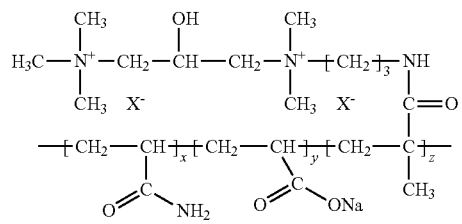

with
x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%,
x+y+z=100%, x, y and z representing the molar percentages of units derived, respectively, from acrylamide, acrylic acid (sodium salt) and DIQUAT.
Other polymers are as follows:

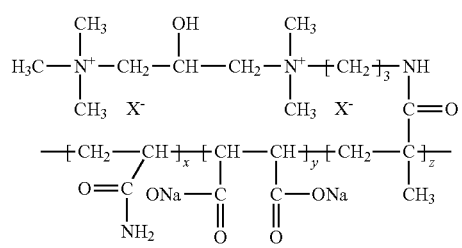

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

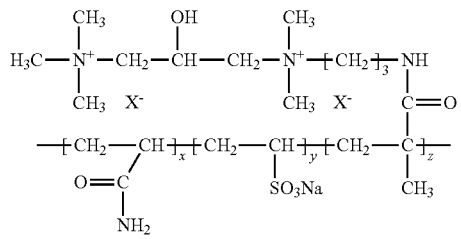

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

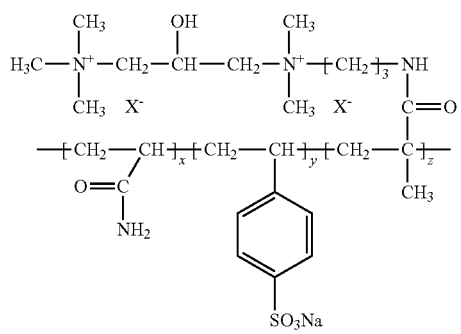

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

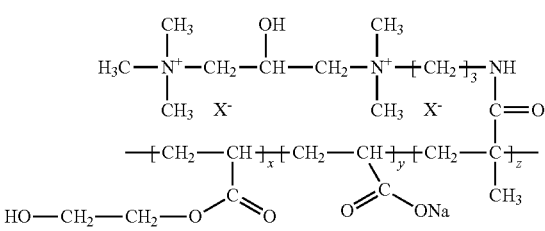

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

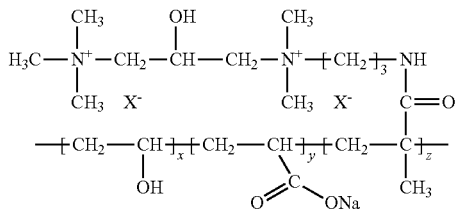

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

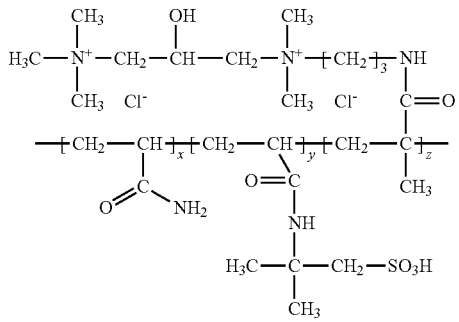

x having a number-average value of from 0 to 50% and preferably from 0 to 30%, preferably equal to 0,
y having a number-average value of from 10% to 95% and preferably from 50% to 70%,
z having a number-average value of from 0.1% to 50% and preferably from 10% to 50%,
the ratio y/z preferably being from about 4/1 to 1/2 and preferably between 4/1 and 1/1,
x+y is from 50% to 99.9%.

The composition advantageously comprises from 0.1% to 5% by weight and preferably from 0.3% to 1.5% by weight of polymer. It is pointed out that the polymer may be introduced into the composition in the form of a more or less concentrated aqueous solution. The amounts mentioned above are amounts expressed as solids.

Cosmetically Acceptable Vector

Any cosmetically acceptable vector allowing the ampholytic polymer to be formulated and making it possible to obtain the desired cosmetic composition form, for the intended use, may be used. Various cosmetically acceptable vectors for different types of formulation are known to those skilled in the art.

Examples of cosmetically acceptable vectors that may be mentioned include aqueous vectors (comprising water), alcoholic vectors (comprising an alcohol, for example ethanol, isopropanol, ethylene glycol or polyethylene glycols), propylene glycol, aqueous-alcoholic vectors (comprising a mixture of water and of an alcohol, for example ethanol, isopropanol, ethylene glycol or polyethylene glycols). Certain volatile or non-volatile oils may also be used. Mention may be made, for example, of fluid silicones, such as cyclopentasiloxane, for example Mirasil CM5 sold by Rhodia.

A person skilled in the art knows how to select the vectors that are suitable for the desired types of formulation, and for the intended uses. For example aqueous vectors are generally used for shampoos or shower gels. A propylene glycol vector may be used for compositions in the form of creams. A cyclomethicone vector may be used for makeup compositions, for example for foundations.

Composition

Surfactants

The composition is an aqueous composition optionally comprising surfactants it may be a mixture of different surfactants. The surfactants included in the composition preferably comprise at least one anionic surfactant. The surfactants may also comprise amphoteric surfactants (true amphoteric or zwitterionic surfactants), neutral surfactants (nonionic surfactants) and/or cationic surfactants. The compositions comprising at least one anionic surfactant and at least one amphoteric surfactant are particularly advantageous, especially for reasons of softness. The total amount of surfactants in the composition is between 0 and 30% by weight.

For compositions intended for treating the hair, for instance shampoos, the surfactant content is advantageously between 10% and 20% by weight. Such composition may comprise salts, for example sodium or ammonium chloride, advantageously in a content of less than 3% by weight.

For compositions intended for treating the skin, for instance shower gels, the surfactant content is advantageously between 5% and 15% by weight. Such compositions also preferably comprise at least 2% by weight of salts, for example sodium or ammonium chloride.

For hair conditioners, the surfactant content may be less than 5% by weight.

The weight proportion of anionic surfactants relative to the total amount of surfactants is preferably greater than 50% and preferentially greater than 70%.

Parameters (pH)

The pH of the composition is greater than or equal to 5.5. It may be, for example, between 5.5 and 7.5 and preferably between 6 and 6.5. The pH obviously depends on the compounds present in the composition. Acidic or basic pH regulators, for example citric acid, or sodium hydroxide, potassium hydroxide or ammonium hydroxide, may obviously be used in the composition.

Nature of the Surfactants

The anionic surfactants may be chosen from the following surfactants:
  alkyl ester sulfonates, for example of formula R—CH(SO$_3$M)-CH$_2$COOR', or alkyl ester sulfates, for example of formula R—CH(OSO$_3$M)-CH$_2$COOR', in which R represents a $C_8$-$C_{20}$ and preferably $C_{10}$-$C_{16}$ alkyl radical, R' a $C_1$-$C_6$ and preferably $C_1$-$C_3$ alkyl radical and M an alkaline-earth metal cation, for example sodium, or an ammonium cation. Mention may be made most particularly of methyl ester sulfonates whose radical R is of $C_{14}$-$C_{16}$;
  alkylbenzenesulfonates, more particularly of $C_9$-$C_{20}$, primary or secondary alkylsulfonates, especially of $C_8$-$C_{22}$, and alkylglyceryl sulfonates;
  alkyl sulfates, for example of formula ROSO$_3$M, in which R represents a $C_{10}$-$C_{24}$ and preferably $C_{12}$-$C_{20}$ alkyl or hydroxyalkyl radical; M represents a cation of the same definition as above;
  alkyl ether sulfates, for example of formula RO(OA)$_n$-SO$_3$M in which R represents a $C_{10}$-$C_{24}$ and preferably $C_{12}$-$C_{20}$ alkyl or hydroxyalkyl radical; OA representing an ethoxylated and/or propoxylated group; M representing a cation of the same definition as above, n generally ranging from 1 to 4, for instance lauryl ether sulfate with n=2;
  alkylamide sulfates, for example of formula RCONHR'OSO$_3$M in which R represents a $C_2$-$C_{22}$ and preferably $C_6$-$C_{20}$ alkyl radical, R' represents a $C_2$-$C_3$ alkyl radical, M representing a cation of the same definition as above, and also the polyalkoxylated (ethoxylated and/or propoxylated) derivatives thereof (alkylamido ether sulfates)
  saturated or unsaturated fatty acid salts, for example those of $C_8$-$C_{24}$ and preferably of $C_{14}$-$C_{20}$ and of an alkaline-earth metal cation, N-acyl N-alkyltaurates, alkylisethionates, alkylsuccinamates and alkylsulfosuccinates, sulfosuccinate monoesters or diesters, N-acyl sarcosinates and polyethoxycarboxylates;
  phosphate monoesters and diesters, for example having the following formula:
  (RO)$_x$—P(=O) (OM)$_{x'}$ in which R represents an alkyl, alkylaryl, arylalkyl or aryl radical, which are optionally polyalkoxylated, x and x' being equal to 1 or 2, on condition that the sum of x and x' is equal to 3, M representing an alkaline-earth metal cation.

The nonionic surfactants may be chosen from the following surfactants:
  alkoxylated fatty alcohols
  alkoxylated triglycerides
  alkoxylated fatty acids
  alkoxylated sorbitan esters
  alkoxylated fatty amines
  alkoxylated bis(1-phenylethyl)phenols
  alkoxylated tris(1-phenylethyl)phenols
  alkoxylated alkylphenols
  products resulting from the condensation of ethylene oxide with a hydrophobic compound resulting from the condensation of propylene oxide with propylene glycol, such as the Pluronic products sold by BASF;
  products resulting from the condensation of ethylene oxide with the compound resulting from the condensation of propylene oxide with ethylenediamine, such as the Tetronic products sold by BASF;
  alkylpolyglycosides, for instance those described in U.S. Pat. No. 4,565,647;
  fatty acid amides, for example of $C_8$-$C_{20}$.

The amphoteric surfactants (true amphoteric surfactants comprising an ionic group and a potentially ionic group of opposite charge, or zwitterionic surfactants simultaneously comprising two opposite charges) may be chosen from the following surfactants:
  betaines in general, especially carboxy betaines, for example lauryl betaine (Mirataine BB from the company Rhodia) or octyl betaine; amidoalkyl betaines, for instance cocamidopropyl betaine (CAPB) (Mirataine BDJ from the company Rhodia Chimie);

sulfobetaines or sultaines, for instance cocamidopropyl hydroxy sultaine (Mirataine CBS from the company Rhodia);

alkylamphoacetates and alkylamphodiacetates, for instance those comprising a coco or lauryl chain (Miranol C2M, C32 and L32 especially, from the company Rhodia);

alkylamphopropionates or alkylamphodipropionates, (Miranol C2M SF);

alkyl amphohydroxypropyl sultaines (Miranol CS).

The cationic surfactants may be chosen from primary, secondary or tertiary, optionally polyethoxylated fatty amine salts, quaternary ammonium salts such as tetraalkylammonium, alkylamidoalkylammonium, trialkylbenzylammonium, trialkylhydroxyalkylammonium or alkylpyridinium chlorides or bromides, imidazoline derivatives and amine oxides of cationic nature.

Examples of useful compositions that may be mentioned include:

the "sodium" compositions for shampoos typically comprising 12% to 16% by weight of sodium alkyl ether sulfate (for example sodium lauryl ether sulfate "SLES") or a mixture of sodium alkyl ether sulfate and of sodium alkyl sulfate (for example sodium lauryl sulfate "SLS"), 1% to 3% of an amphoteric surfactant (for example cocoamidopropyl betaine "CAPB"), 0.5% to 2% of a salt (for example sodium chloride);

the "ammonium" compositions for shampoos typically comprising 12% to 16% by weight of ammonium alkyl ether sulfate (for example ammonium lauryl ether sulfate "ALES") or of a mixture of ammonium alkyl ether sulfate and of ammonium alkyl sulfate (for example ammonium lauryl sulfate "ALS"), 1% to 3% of an amphoteric surfactant (for example cocoamidopropyl betaine "CAPB"), 0 to 2% of a salt (for example ammonium chloride);

the "sodium" compositions for shower gels typically comprising 6% to 10% by weight of sodium alkyl ether sulfate (for example sodium lauryl ether sulfate "SLES") or of a mixture of sodium alkyl ether sulfate and of sodium alkyl sulfate (for example sodium lauryl sulfate "SLS"), 1% to 3% of an amphoteric surfactant (for example cocoamidopropyl betaine "CAPB"), 2% to 4% of a salt (for example sodium chloride);

the "ammonium" compositions for shower gels typically comprising 6% to 10% by weight of ammonium alkyl ether sulfate (for example ammonium lauryl ether sulfate "ALES") or a mixture of ammonium alkyl ether sulfate and of ammonium alkyl sulfate (for example ammonium lauryl sulfate "ALS"), 1% to 3% of an amphoteric surfactant (for example cocoamidopropyl betaine "CAPB"), 0 to 4% of a salt (for example ammonium chloride).

Other Compounds

The composition may comprise any other compound used in cosmetic compositions intended to be rinsed out (shampoo, shower gel, conditioner, etc.) or not intended to be rinsed out.

Examples that may be mentioned include sequestering agents, softeners, foam modifiers, colorants, nacreous agents (pearlizers), moisturizers, antidandruff or antiseborrheic agents, suspension agents, emulsifiers, ceramides, pseudoceramides, electrolytes, fatty acids, fatty acid esters, hydroxy acids, thickeners, fragrances, preserving agents, organic or mineral sunscreens, proteins, vitamins, polymers, "polyorganosiloxane" silicones, stabilizers and/or conditioning agents and/or conditioning aids, other than the ampholytic copolymer and the polyorganosiloxanes, especially polymers. Some of these compounds are detailed below.

Stabilizer and/or Conditioning Agent and/or Conditioning Aid

The cosmetic composition according to the invention may advantageously comprise at least one stabilizer and/or conditioning agent and/or conditioning aid. These are also occasionally referred to as suspension agents. The term "conditioning aid" means that the presence of the agent improves the conditioning associated with other compounds, for example silicone oils. The agents are understood as being different from the polyorganosiloxane of formula (I). Such agents are known to those skilled in the art. The composition according to the invention may comprise several of these agents (mixtures of combinations), to combine their effects and/or create synergism. Moreover, certain agents may exert several functions. This is the case, for example, for polysaccharides, and cationic derivatives thereof, for example cationic guar derivatives.

The weight proportion of such agents may typically be from 0.1% to 10% by weight and preferably from 0.3% to 8% by weight for polysaccharides or other agents.

As examples of stabilizers that are particularly useful for compositions comprising polyorganosiloxanes, mention may be made of:

crosslinked polyacrylates, for example polymers of Carbopol or Carbomer type sold by BF Goodrich or Noveon, Acritamer sold by Rita or Tego Carbomer sold by Goldschmidt. These compounds may be typically present in an amount of from 0.1% to 3% and preferably from 0.3% to 2% by weight relative to the composition;

the acrylate/aminoacrylate/PEG-20 $C_{10}$-$C_{30}$ alkyl itaconate copolymers sold by National Starch under the name Structure Plus. These compounds may typically be present in an amount of from 0.1% to 3% and preferably from 0.3% to 2% by weight relative to the composition;

insoluble solids forming a network in the composition. These may be fatty acid monoesters or diesters of ethylene glycol, the fatty acids preferably being of $C_{16}$-$C_{18}$. It may be in particular ethylene glycol distearate (EGDS), for example sold by Rhodia as a concentrate with other ingredients under the name Mirasheen. This compound may typically be present in an amount of from 3% to 10% and preferably from 5% to 8% by weight relative to the composition.

Mention may also be made of viscosifiers, gelling agents or texturing agents, for instance anionic acrylic copolymers of Aculyne type sold by ISP or Rohm & Haas, polysaccharides and the noncationic derivatives thereof, such as cellulose derivatives, for instance hydroxypropylcellulose, carboxymethylcellulose, nonionic guar derivatives, for instance hydroxypropyl guar (for example the Jaguar HP products sold by Rhodia), locust bean gum, tara gum or cassia gum, xanthan gum (for example the Rhodicare products sold by Rhodia), succinoglycans (for example Rheozan sold by Rhodia), alginates, carrageenans, chitin derivatives or any other polysaccharide with a texturing function. These polysaccharides and derivatives thereof may be incorporated alone or in synergistic combination with other polysaccharides. These compounds may typically be present in an amount of from 0.1% to 3% and preferably from 0.3% to 1% by weight relative to the composition.

Examples of stabilizers and/or conditioning agents and/or conditioning aids that may be mentioned include:
- cationic polymers derived from polysaccharides, for example cationic cellulose derivatives, cationic starch derivatives, cationic guar derivatives and cationic locust bean gum derivatives,
- synthetic cationic polymers,
- mixtures or combinations of these agents.

The synthetic or nonsynthetic cationic polymers that can act as conditioning agent are especially polymers of polyquaternium type, for instance polyquaternium-1, polyquaternium-2, polyquaternium-4, polyquaternium-5, polyquaternium-6 (also known as Merquat 1000 available from Nalco), polyquaternium-7 (also known as Merquat 5500 available from Nalco), polycuaternium-8, polyquaternium-9, polyquaternium-10 (also known as Polymer JR 400, sold by Amerchol), polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22 (also known as Merquat 280, 281 and 298 available from Nalco), polyquaternium-24, polyquaternium-27, polyquaternium-28, polyquaternium-29 (also known as Kytamer KCO available from Amerchol), polyquaternium-30, polyquaternium-31, polyquaternium-32, polyquaternium-33, polyquaternium-34, polyquaternium-35, polyquaternium-36, polyquaternium-37, polyquaternium-39 (also known as Merquat 3300 and 3331 available from Nalco), polyquaternium-44, polyquaternium-27 (also known as Merquat 2001 available from Nalco) and polyquaternium-55.

As mentioned above, the composition may comprise other synthetic or natural polymers or polymers derived from biological preparation processes, which are functionalized, where appropriate, for example with cationic or neutral groups. These polymers may have a stabilizing or structuring action on the compositions, and/or a conditioning action (deposition on the surface of the skin or the hair).

Examples that may be mentioned include cationic polysaccharide derivatives, for instance guar or cellulose derivatives. Cationic polymers functionalized with hydrophobic groups, for instance C1-C14 and preferably C2-C8 alkyl chains, optionally containing a hydroxyl group, may be used. These hydrophobic groups are attached to the main polymer chain via ether bonds.

Moreover, and in the case of hydrophobic or nonhydrophobic modified cationic guars, the cationic group is a quaternary ammonium group bearing three radicals, which may be identical or different, chosen from hydrogen, an alkyl radical containing 1 to 22 carbon atoms, more particularly 1 to 14 and advantageously 1 to 3 carbon atoms. The counterion is a halogen, preferably chlorine.

In the case of hydrophobic or nonhydrophobic modified cationic celluloses, the cationic group is a quaternary ammonium group bearing three radicals, which may be identical or different, chosen from hydrogen and an alkyl radical containing 1 to 10 carbon atoms, more particular 1 to 6 and advantageously 1 to 3 carbon atoms. The counterion is a halogen, preferably chlorine.

Among the cationic guar derivatives that may be mentioned are guar hydroxypropyl trimonium chloride (Jaguar C13S, C14S, or C17, Jaguar Excel and Jaguar C 2000 sold by the company Rhodia Chimie) or hydroxypropyl guar hydroxypropyl trimonium chloride (Jaguar C162 sold by Rhodia).

Among the cationic cellulose derivatives that may be used are trimethylammonium-3-propyl cellulose poly(1,2-oxyethanediyl)-2-hydroxy ether chloride or polyquaternium-10, for instance Polymer JR400 (INPI name: PQ10) sold by the company Amerchol.

Nonionic polysaccharide derivatives, for example hydroxypropyl guar, may also be used.

Synthetic polymers, and more particularly homopolymers such as polymethacrylamidopropyl trimonium chloride (Polycare 133 sold by the company Rhodia Chimie), may also be suitable.

The cationic polymers more particularly have a weight-average molar mass of at least 2000 g/mol and more preferably between $2\times10^4$ and $3\times10^6$ g/mol, depending on their possible degree of polymerization. The weight-average molar masses of the polymers are usually measured by size exclusion. They may optionally be measured directly by light scattering or from the intrinsic viscosity using a calibration, according to: "Viscosity-Molecular weight relationship, intrinsic chain flexibility and dynamic solution properties of guar galactomannan" by G. Robinson, S. B. Ross Murphy, E. R. Morris, Carbohydrate Research 107, p. 17-32, 1982.

In the case of cationic polysaccharide derivatives, the degree of hydroxyalkylation (molar substitution or MS) is preferably between 0 and 1.2. Still in the case of these polymers, the degree of cationicity (degree of substitution or DS) is more particularly between 0.01 and 0.6. This is the case, for example, for the Jaguar C162 and C2000 products sold by the company Rhodia Chimie.

Polyorganosiloxanes (Silicone)

The composition may comprise a silicone (silicone oil). The terms "silicone" and "poly-organosiloxane" mean any organosiloxane compound comprising alkyl (for example methyl) groups and/or functionalized with groups other than alkyl groups.

The polyorganosiloxane is advantageously (in shampoos and conditioners in particular) a nonvolatile and water-insoluble polyorganosiloxane. It advantageously has a viscosity of between 1000 and 2 000 000 mPa·s and preferably between 5000 and 500 000 mPa·s. The polyorganosiloxane may especially be a polydimethylorganosiloxanesiloxane ("PDMS", INCI name: dimethicone) or a polyorganosiloxane containing amine (for example amodimethicone according to the INCI name), quaternary ammonium (for example the silicone quaternum 1 to 10 products according to the INCI name) hydroxyl (terminal or non-terminal) or polyoxyalkylene groups, for example polyethylene oxide and/or polypropylene oxide (as end groups, as a block within a PDMS chain, or as grafts), or several of these groups.

The amount of polyorganosiloxane present in the composition may typically be from 0.1% to 5% by weight, for example from 0.5% to 1.5% or 2%.

The polyorganosiloxane (silicones) is (are) preferably present in the composition in emulsion form (liquid droplets of silicone dispersed in the aqueous phase). The emulsion may especially be an emulsion whose mean droplet size is greater than or equal to 2 µm, and/or whose mean droplet size is greater than or between 0.15 µm and 2 µm, or whose mean droplet size is less than or equal to 0.15 µm.

The droplets of the emulsion may be of relatively large or small size. Reference may thus be made to microemulsions, miniemulsions or macroemulsions. In the present patent application, the term "emulsion" especially covers all these types of emulsion. Without wishing to be bound to any theory, it is pointed out that microemulsions are generally thermodynamically stable systems generally comprising large amounts of emulsifiers. The other emulsions are generally systems in thermodynamically unstable state, conserving for a certain time, in metastable state, the mechanical energy supplied during the emulsification. These systems generally comprise smaller amounts of emulsifiers.

The emulsions may be obtained by mixing the vector, preferably an aqueous vector, the polyorganosiloxane and in general an emulsifier, followed by emulsification. This may be referred to as in situ emulsification.

The compositions in emulsion form may also be obtained by mixing the vector, preferably an aqueous vector, with an emulsion prepared beforehand of droplets comprising the polyorganosiloxane in an external phase, which is preferably miscible with the cosmetically acceptable vector, preferably of the same nature as said vector, preferably an aqueous vector. This embodiment may be preferred since it is simple to perform. In addition, this embodiment is particularly suitable for preparing cosmetic compositions in which the organopolysiloxane is in microemulsion form. This may be referred to as prior emulsification.

According to one particular embodiment, the emulsion is a microemulsion whose droplet size is less than 0.15 µm. In this embodiment, the composition preferably comprises a proportion of greater than 10% by weight and preferably at least 15% by weight of emulsifier relative to the weight of polyorganosiloxane.

The size of the microemulsion droplets may be measured on an emulsion prepared prior to its introduction into the cosmetic composition, by dynamic light scattering (DQEL), for example as described below. The apparatus used consists, for example, of a Spectra-Physics 2020 laser, a Brookhaven 2030 correlator and the associated computer-based equipment. Since the sample is concentrated, it is diluted in deionized water and filtered through a 0.22 µm filter to have a final concentration of 2% by weight. The diameter obtained is an apparent diameter. The measurements are taken at angles of 90° and 135°. For the size measurements, besides the standard analysis with cumulents, three exploitations of the autocorrelation function are used (exponential sampling or EXP-SAM described by Prof. Pike, the "Non Negatively Constrained Least Squares" or NNLS method, and the CONTIN method described by Prof. Provencher), which each give a size distribution weighted by the scattered intensity, rather than by the mass or the number. The refractive index and the viscosity of the water are taken into account.

According to one advantageous mode, the microemulsion is transparent. The microemulsion may have, for example, a transmittance of at least 90% and preferably of at least 95% at a wavelength of 600 nm, for example measured using a Lambda 40 UV-visible spectrometer, at a concentration of 0.5% by weight in water. In this context, the cosmetic composition may advantageously be transparent. It may have, for example, a transmittance of at least 90% and preferably of at least 95% at a wavelength of 600 nm, measured, for example, using a Lambda 40 UV-visible spectrometer.

According to another particular embodiment, the emulsion is an emulsion whose mean droplet size is greater than or equal to 0.15 µm, for example greater than 0.5 µm, or 1 µm, or 2 µm, or 10 µm, or 20 µm, and preferably less than 100 µm. The droplet size may be measured on an emulsion prepared prior to its introduction into the cosmetic composition, or directly on the cosmetic composition diluted in water, by optical microscopy and/or laser granulometry (Horiba LA-910 laser scattering analyzer). In this embodiment, the composition preferably comprises a proportion of less than 10% by weight of emulsifier relative to the weight of polyorganosiloxane.

Emulsifiers that are useful for preparing the polyorganosiloxane emulsion are especially nonionic surfactants, preferably polyalkoxylated, for example chosen from alkoxylated fatty alcohols, alkoxylated triglycerides, alkoxylated fatty acids, alkoxylated sorbitan esters, alkoxylated fatty amines, alkoxylated bis(1-phenylethyl)phenols, alkoxylated tris(1-phenylethyl)phenols and alkoxylated alkylphenols, in which the number of alkoxy and more particularly oxyethylene and/or oxypropylene units is such that the HLB value is greater than or equal to 10.

Among the water-soluble silicone derivatives in the composition that may be mentioned, inter alia, are dimethicone copolyols (Mirasil DMCO sold by the company Rhodia Chimie).

As regards the silicones that are in the form of dispersions insoluble in the water of the composition, water-insoluble and nonvolatile organopolysiloxanes may suitably be used, among which mention may be made of polyalkylsiloxane, polyarylsiloxane and polyalkylarylsiloxane oils, gums or resins, or water-insoluble functionalized derivatives thereof, or mixtures thereof, which are nonvolatile.

Said organopolysiloxanes are considered as water-insoluble and nonvolatile when their solubility in water is less than 50 g/liter and their intrinsic viscosity is at least 3000 mPa·s at 25° C.

Examples of water-insoluble and nonvolatile organopolysiloxanes or silicones that may be mentioned include silicone gums, for instance the diphenyl dimethicone gum sold by the company Rhodia Chimie, and preferably polydimethylsiloxanes with a viscosity at least equal to $6\times10^5$ mPa·s at 25° C., even more preferably those with a viscosity of greater than $2\times10^6$ mPa·s at 25° C., such as Mirasil DM 500 000® sold by the company Rhodia Chimie.

According to the invention, the water-insoluble and nonvolatile organopolysiloxane or silicone is in a form dispersed in the cosmetic composition containing it.

Said organopolysiloxane or silicone is in the form of particles or droplets whose size may be chosen as a function of the nature of the cosmetic composition or of the desired performance for said composition. In general, this size may range from 0.01 to 70 microns.

Preferably, this size is from about 0.1 to 50 microns and most particularly from about 1 to 30 microns.

To facilitate their implementation, these organopolysiloxanes may be dispersed or dissolved beforehand in volatile or nonvolatile low-viscosity silicone derivatives, and then emulsified in the cosmetic composition.

Among these low-viscosity silicones that may be mentioned are volatile cyclic silicones and polydimethylsiloxanes of low mass.

Functionalized silicone derivatives, for instance amino derivatives, may also be used, directly in the form of emulsions or starting with a preformed microemulsion. They may be compounds known under the term "amino silicones" or "hydroxylated silicones". Mention is made of Mirasil ADM-E (amodimethicone) sold by the company Rhodia, and dimethiconol.

As polyorganosiloxanes that may be used, mention is made especially of:
  polyorganosiloxanes comprising —Si(CH$_2$)$_2$O— units and —SiY(CH$_2$)O— units in which Y is a —(CH$_2$)$_3$—NH(CH$_2$)$_2$—NH$_2$ or —(CH$_2$)$_3$—NH$_2$ group
  polyorganosiloxanes comprising —Si(CH$_2$)$_2$O— units and —HO—Si(CH$_2$)$_2$O— terminal units and/or —Si(CH$_2$)(OH)O— non-terminal units
  polyorganosiloxanes comprising —Si(CH$_2$)$_2$O— units and —SiY(CH$_2$)O— units in which Y is -L$^X$-Z$^X$-Palc in which L$^X$ is a divalent bonding group, preferably an alkyl group, Z$^X$ is a covalent bond or a divalent joint group comprising a hetero atom, Palc is a group of formula [OE]$_s$-[OP]$_t$—X', in which OE is a group of formula —CH$_2$—CH$_2$—O—, OP is a group of formula —CH$_2$—CHCH$_3$—O— or —CHCH$_3$—CH$_2$—O—, X' is a hydrogen atom or a hydrocarbon-based group, s is an average number greater than 1, and t is an average number greater than or equal to 0, polyorganosiloxanes whose chain comprises at least one block comprising units having the formula of the units —Si(CH$_2$)$_2$O— and at least one —[OE]$_s$-[OP]$_t$—block, polyorganosiloxanes comprising —Si(CH$_2$)$_2$O— units and/or —Si(CH$_2$)RO— and/or —SiR$_2$O— and/or R—Si(CH$_2$)$_2$O— and/or H$_3$C—SiR$_2$O— and/or R—SiR$_2$O— units in which R, which may be identical or different, is an alkyl group other than a methyl group, an aryl group, an alkyl group, alkylaryl group or an aralkyl group.

Other Compounds

It may similarly be envisioned to use oils that may have conditioning, protective or emollient functions. Such oils are generally chosen from alkylmonoglycerides, alkyldiglycerides, triglycerides, for instance oils extracted from plants and vegetables (palm oil, coconut oil, cottonseed oil, soybean oil, sunflower oil, olive oil, grapeseed oil, sesame seed oil, groundnut oil, castor oil, etc.) or oils of animal origin (tallow, fish oils, etc.), derivatives of these oils, for instance hydrogenated oils, lanolin derivatives, petrolatum, mineral oils or liquid paraffins, perhydrosqualane, squalene, diols, for instance 1,2-dodecanediol, cetyl, alcohol, stearyl alcohol, oleyl alcohol, fatty esters, for instance isopropyl palmitate, 2-ethylhexyl cocoate, myristyl myristate, and lactic acid, stearic acid, behenic acid or isostearic acid esters.

Bactericidal or fungicidal agents may also be incorporated into the cosmetic composition, in the form of dispersions or solutions, in order to improve the skin disinfection, for instance triclosan; antidandruff agents, especially such as zinc pyrithione or octopyrox; insecticidal agents, for instance natural or synthetic pyrethroids.

The cosmetic composition may also contain agents for protecting the skin and/or the hair against attack from sunlight and UV rays. Thus, the compositions may comprise sunscreens, which are chemical compounds that strongly absorb UV radiation, for instance the compounds permitted in European directive No. 76/768/EEC, its appendices and the subsequent modifications of this directive.

When the various components constituting the cosmetic composition are of excessively low solubility in the composition or when they are in solid form at room temperature, said constitutive components may advantageously be dissolved in an organic vehicle, for instance in mineral or natural oils, silicone derivatives or waxes, or alternatively may be encapsulated in matrices, for instance polymers of latex type.

The cosmetic compositions forming the subject of the invention may also contain fixative resins.

When they are present, these fixative resins are generally present in concentrations of between 0.01% and 10% and preferably between 0.5% and 5%.

The fixative resins included in the cosmetic compositions are more particularly chosen from the following resins:

methyl acrylate/acrylamide copolymers, polyvinyl methyl ether/maleic anhydride copolymers, vinyl acetate/crotonic acid copolymers, octylacrylamide/methyl acrylate/butylaminoethyl methacrylate copolymers, polyvinylpyrrolidones, polyvinylpyrrolidone/methyl methacrylate copolymers, polyvinylpyrrolidone/vinyl acetate copolymers, polyvinyl alcohols, polyvinyl alcohol/crotonic acid copolymers, polyvinyl alcohol/maleic anhydride copolymers, hydroxypropylcelluloses, hydroxypropyl guars, sodium polystyrenesulfonates, polyvinylpyrrolidone/ethyl methacrylate/methacrylic acid terpolymers, poly(methyl vinyl ether/maleic acid) monomethyl ethers, polyvinyl acetates grafted onto polyoxyethylene trunks (EP-A-219 048), copolyesters derived from a terephthalic and/or isophthalic and/or sulfoisophthalic acid, anhydride or diester and from a diol, such as:

polyester copolymers based on ethylene terephthalate and/or propylene terephthalate and polyoxyethylene terephthalate units (U.S. Pat. No. 3,959,230, U.S. Pat. No. 3,893,929, U.S. Pat. No. 4,116,896, U.S. Pat. No. 4,702,857, U.S. Pat. No. 4,770,666);

sulfonated polyester oligomers obtained by sulfonation of an oligomer derived from ethoxylated allylic alcohol, dimethyl terephthalate and 1,2-propylene diol (U.S. Pat. No. 4,968,451);

polyester copolymers derived from dimethyl terephthalate, isophthalic acid, dimethyl sulfoisophthalate and ethylene glycol (EP-A-540 374);

copolymers comprising polyester units derived from dimethyl terephthalate, isophthalic acid, dimethyl sulfoisophthalate and ethylene glycol and from polyorganosiloxane units (FR-A-2 728 915);

sulfonated polyester oligomers obtained by condensation of isophthalic acid, dimethyl sulfosuccinate and diethylene glycol (FR-A-2 236 926);

polyester copolymers based on propylene terephthalate and polyoxyethylene terephthalate units and ending with methyl or ethyl units (U.S. Pat. No. 4,711,730) or polyester oligomers ending with alkylpolyethoxy groups (U.S. Pat. No. 4,702,857) or sulfopolyethoxy anionic groups (U.S. Pat. No. 4,721,580), and sulfoaroyls (U.S. Pat. No. 4,877,896);

polyester-polyurethanes obtained by reacting a polyester obtained from adipic acid and/or terephthalic acid and/or sulfoisophthalic acid and from a diol, with a prepolymer containing isocyanate end groups obtained from a polyoxyethylene glycol and from a diisocyanate (FR-A-2 334 698);

ethoxyolated monoamines or polyamines, and ethoxylated amine polymers (U.S. Pat. No. 4,597,898, EP-A-11 984).

Preferably, the fixative resins are chosen from polyvinylpyrrolidone (PVP), copolymers of polyvinylpyrrolidone and of methyl methacrylate, copolymer of polyvinylpyrrolidone and of vinyl acetate (VA), polyethylene glycol terephthalate/polyethylene glycol copolymers, polyethylene glycol terephthalate/polyethylene glycol/sodium polyisophthalate sulfonate copolymers, and mixtures thereof.

These fixative resins are preferably dispersed or dissolved in the chosen vehicle.

The cosmetic compositions forming the subject of the invention may also contain polymer derivatives having a protective function.

These polymer derivatives may be present in amounts from about 0.01-10%, preferably about 0.1-5% and most particularly about 0.2-3% by weight.

These agents may be chosen especially from:

nonionic cellulose-based derivatives such as cellulose hydroxy ethers, methylcellulose, ethylcellulose, hydroxypropylmethylcellulose and hydroxybutylmethylcellulose;

polyvinyl esters grafted onto polyalkylene trunks, such as polyvinyl acetates grafted onto polyoxyethylene trunks (EP-A-219 048);

polyvinyl alcohols.

The cosmetic compositions forming the subject of the invention may also comprise plasticizers.

Said plasticizers, when they are present, may represent between 0.1% and 20% and preferably from 1% to 15% of the formulation.

Among the plasticizers that are particularly useful, mention may be made of adipates, phthalates, isophthalates, azelates, stearates, silicone copolyols, glycols and castor oil, or mixtures thereof.

Metal-sequestering agents, more particularly those that sequester calcium, for instance citrate ions, may also advantageously be added to these compositions.

Humectants may also be incorporated into the cosmetic compositions forming the subject of the invention, among which are, inter alia, glycerol, sorbitol, urea, collagen, gelatin, aloe vera, hyaluronic acid or volatile water-soluble solvents, for instance ethanol or propylene glycol, the contents of which may be up to 60% by weight of the composition.

To further reduce the irritation or attack of the scalp, water-soluble or water-dispersible polymers may also be added, for instance collagen or certain non-allergenic derivatives of animal or plant proteins (for example wheat protein hydrolyzates), natural hydrocolloids (guar gum, locust bean gum, tara gum, etc.) or hydrocolloids derived from fermentation processes, and derivatives of these polycarbohydrates, for instance modified nonionic celluloses, for instance hydroxyethylcellulose, or modified anionic celluloses, for instance carboxymethylcellulose; guar derivatives or locust bean gum derivatives, for instance the nonionic derivatives thereof (for example hydroxypropyl guar) or the anionic derivatives thereof (carboxymethyl guar and carboxymethylhydroxypropyl guar).

Mineral powders or particles, for instance calcium carbonate, sodium bicarbonate, calcium dihydrogen phosphate, mineral oxides in powder form or in colloidal form (particles less than about 1 micrometer in size, occasionally a few tens of nanometers), for instance titanium dioxide, silica, aluminum salts generally used as antiperspirants, kaolin, talc, clays and derivatives thereof, etc., may be added in combination to these compounds.

Preserving agents, for instance methyl, ethyl, propyl and butyl esters of p-hydroxybenzoic acid, sodium benzoate, Germaben® or any chemical agent for preventing the proliferation of bacteria or molds that is conventionally used in cosmetic compositions may also be introduced into the aqueous cosmetic compositions according to the invention, generally to a proportion of from 0.01% to 3% by weight.

The amount of these products is usually adjusted to prevent any proliferation of bacteria, molds or yeasts in the cosmetic compositions.

As an alternative to these chemical agents, it may occasionally be possible to use agents that modify the water activity and that greatly increase the osmotic pressure, for instance carbohydrates or salts.

To protect the skin and/or the hair against attack from sunlight and UV rays, organic or mineral sunscreens may be added to the compositions, for example mineral particles, for instance zinc oxide, titanium dioxide or cerium oxides, in powder form or in the form of colloidal particles, alone or as a mixture. These powders may optionally be surface-treated to increase the efficacy of their anti-UV action or to facilitate their incorporation into the cosmetic formulations, or to prevent surface photoreactivity. The organic sunscreens may especially be introduced into the polyorganosiloxane, if it is present in the composition.

One or more fragrances, colorants chosen from, among which mention may be made of the products described in appendix IV ("List of colouring agents allowed for use in cosmetic products") of European directive No. 76/768/EEC of 27 Jul. 1976, known as the Cosmetic Directive, and/or opacifiers, for instance pigments, may be added to these ingredients, if necessary, with the aim of increasing the comfort during the use of the composition by the consumer.

Although this is not obligatory, the composition may also contain viscosifying or gelling polymers so as to adjust the texture of the composition, for instance the crosslinked polyacrylates (Carbopol sold by Goodrich) already mentioned above, noncationic cellulose derivatives, for instance hydroxypropylcellulose or carboxymethylcellulose, guars and nonionic derivatives thereof, xanthan gum and its derivatives, used alone or in combination, or the same compounds, generally in the form of water-soluble polymers modified with hydrophobic groups covalently bonded to the polymer skeleton, as described in patent WO 92/16187 and/or water to bring the total of the constituents of the formulation to 100%.

The cosmetic compositions forming the subject of the invention may also contain polymeric dispersants in an amount of about 0.1-7% by weight, to control the calcium and magnesium hardness, these being agents such as:

water-soluble polycarboxylic acid salts with a weight-average molecular mass of about from 2000 to 100 000 g/mol, obtained by polymerization or copolymerization of ethylenically unsaturated carboxylic acids such as acrylic acid, maleic acid or anhydride, fumaric acid, itaconic acid, aconitic acid, mesaconic acid, citraconic acid or methylenemalonic acid, and most particularly polyacrylates with a weight-average molecular mass of about from 2000 to 10 000 g/mol (U.S. Pat. No. 3,308,067), copolymers of acrylic acid and of maleic anhydride with a weight-average molecular mass of about from 5000 to 75 000 g/mol (EP-A-66 915);

polyethylene glycols with a weight-average molecular mass of about from 1000 to 50 000 g/mol.

Other details or advantages of the invention will emerge more clearly in the light of the examples that follow, which are given without any limiting nature.

EXAMPLES

Compositions comprising ingredients chosen from the following are prepared:

| Ingredient | Type | Compound |
|---|---|---|
| SLES | Anionic surfactant | Sodium lauryl ether sulfate (2EO), Empicol ESB/3 M sold by Hunstman |
| SLS | Anionic surfactant | Sodium lauryl sulfate |
| ALES | Anionic surfactant | Ammonium lauryl ether sulfate (2EO), Rhodapex-EA-2 sold by Rhodia |
| ALS | Anionic surfactant | Ammonium lauryl sulfate, Rhodapon L-22 sold by Rhodia |
| CAPB | Amphoteric surfactant | Cocoamidopropyl betaine, Mirataine BET-C-30 sold by Rhodia |
| Salt | | Sodium chloride or ammonium chloride |
| Polymer A | | Copolymer comprising 33% by number of units derived from DIQUAT and 67% by number of units derived from acrylic acid, with a molecular mass of about 1 000 000 |
| Polymer B | | Copolymer comprising 50% by number of units derived from DIQUAT and 50% by number of units derived from acrylic acid, with a molecular mass of about 1 000 000 |
| Polymer C | Cationic polymer | Cationic cellulose: JR 400 sold by Amerchol - INCI PQ10 |

| Ingredient | Type | Compound |
|---|---|---|
| Polymer D | Cationic polymer | Cationic guar: Jaguar C13S: sold by Rhodia |
| Polymer E | Cationic polymer | Jaguar C162: sold by Rhodia |
| Silicone 1 | Conditioning agent | Mirasil DME-2 sold by Rhodia: dimethicone (PDMS) emulsion with a viscosity of about 500 000 cP and a droplet size of about 2 μm, stabilized with succinoglycan |
| Silicone 2 | Conditioning agent | Mirasil DME-30 sold by Rhodia: dimethicone (PDMS) emulsion with a viscosity of about 500 000 cP and a droplet size of about 2 μm, stabilized with succinoglycan |

Procedure

1. Mix the water and the polymer
2. Add the CAPB
3. Add the anionic surfactant, optionally followed by the silicone emulsion
4. Adjust the pH to 6-6.5 by adding sodium hydroxide or citric acid
5. Add the salt The following compounds, the weight amount of each ingredient of which is given below, are prepared (the letter C indicates comparative examples):

| | Example | | | | | | | | | | |
|---|---|---|---|---|---|---|---|---|---|---|---|
| | 1 | 2 | 3 | 4C | 5 | 6 | 7 | 8C | 9 | 10 | 11C |
| SLES (%) | 14 | 14 | 14 | 14 | / | / | / | / | 8 | 8 | 8 |
| SLS (%) | / | / | / | / | / | / | / | / | / | / | / |
| ALES (%) | / | / | / | / | 7 | 7 | 7 | 7 | / | / | / |
| ALS (%) | / | / | / | / | 7 | 7 | 7 | 7 | / | / | / |
| CAPB (%) | 2 | 2 | 2 | 2 | 2 | 2 | 2 | 2 | 2 | 2 | 2 |
| NH$_4$Cl (%) | / | / | / | / | 0.25 | / | / | 0.25 | / | / | / |
| NaCl (%) | 1.5 | 1.5 | 1.5 | 1.5 | / | / | / | / | 3 | 3 | 3 |
| Polymer A (%) | 0.3 | 1 | / | / | 0.3 | 1 | / | / | 0.5 | 0.5 | / |
| Polymer B (%) | / | / | 1 | / | / | / | 1 | / | / | / | / |
| Water | Up to 100% | | | | | | | | | | |

| | 12 | 13 | 14 | 15C | 16C | 17C | 18C | 19C | 20C |
|---|---|---|---|---|---|---|---|---|---|
| SLES (%) | 14 | 14 | 14 | 14 | 14 | 14 | 14 | 14 | 14 |
| CAPB (%) | 2 | 2 | 2 | 2 | 2 | 2 | 2 | 2 | 2 |
| NaCl (%) | 1.5 | 1.5 | 1.5 | 1.5 | 1.5 | 1.5 | 1.5 | 1.5 | 1.5 |
| Polymer A (%) | 0.1 | 0.2 | 0.3 | / | / | / | | | |
| Polymer C (%) | | | | 0.1 | 0.2 | 0.3 | | | |
| Polymer E (%) | | | | | | | 0.1 | 0.2 | 0.3 |
| Silicone 1 (% solids) | 1 | 1 | 1 | 1 | 1 | 1 | 1 | 1 | 1 |
| Silicone 2 (% solids) | / | / | / | / | / | / | / | / | / |
| Water | Up to 100% | | | | | | | | |

| | Example | | | | | |
|---|---|---|---|---|---|---|
| | 21 | 22C | 23C | 24C | 25C | 26C |
| SLES (%) | 14 | 14 | 14 | 14 | 14 | 14 |
| CAPB (%) | 2 | 2 | 2 | 2 | 2 | 2 |
| NaCl (%) | 1.5 | 1.5 | 1.5 | 1.5 | 1.5 | 1.5 |
| Polymer A (%) | 0.2 | / | / | / | / | / |
| Polymer C (%) | | 0.2 | | | | |
| Polymer D (%) | | | 0.2 | | | |
| Polymer E (%) | / | / | / | 0.1 | 0.2 | 0.3 |
| Silicone 1 (% solids) | / | / | / | | | |
| Silicone 2 (% solids) | 1 | 1 | 1 | | | |
| Water | Up to 100% | | | | | |

| | Example | | | | | |
|---|---|---|---|---|---|---|
| | 27 | 28 | 29 | 30C | 31C | 32C |
| SLES (%) | 14 | 14 | 14 | 14 | 14 | 14 |
| CAPB (%) | 2 | 2 | 2 | 2 | 2 | 2 |
| NaCl (%) | 1.5 | 1.5 | 1.5 | 1.5 | 1.5 | 1.5 |
| Polymer A (%) | 0.1 | 0.2 | 0.3 | / | / | / |
| Polymer C (%) | | | | 0.1 | 0.2 | 0.3 |
| Polymer D (%) | | | | | | |
| Silicone 1 (% solids) | / | / | / | / | / | / |

| | -continued | | | | | |
|---|---|---|---|---|---|---|
| Silicone 2 (% solids) | / | / | / | / | / | / |
| Water | | | Up to 100% | | | |

The transmittance (transparency) of the compositions is measured at 600 nm using a spectrophotometer (Jasco 7800) in 10×10 mm cells or in 10×100 mm cells. The Brookfield viscosity of the compositions is measured using a Brookfield DV-I viscometer, at 22° C., 10 rpm, spindle 4 for viscosities of less than 11 000 mPa·s, spindle 5 for viscosities of from 11 000 to 30 000 mPa·s and spindle 6 above that.

| | Example | | | | | | | | |
|---|---|---|---|---|---|---|---|---|---|
| | 30C | 31C | 32C | 24C | 25C | 26C | 27 | 28 | 29 |
| Transmittance 10 × 10 mm | 99 | 99 | 99 | 98 | 95 | 92 | 98 | 95 | 94 |
| Transmittance 10 × 100 mm | 90 | 90 | 88 | 76 | 55 | 41 | 75 | 65 | 54 |

The invention claimed is:

1. A process for the treatment of skin or hair, comprising the step of treating said skin or hair with an efficient cleaning or rinsing amount of a composition comprising a cosmetically acceptable vector, optionally a surfactant, and an ampholytic copolymer comprising cationic units (c) and anionic or potentially anionic units (a), wherein:
 the copolymer comprises:
  0.1% to 50% by number of units (c) derivable from the polymerization of at least one monomeric compound (c) of formula:

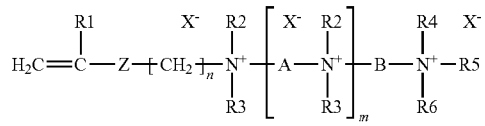

wherein:
  $R_1$ comprises a hydrogen atom or a methyl or ethyl group;
  $R_2, R_3, R_4, R_5$ and $R_6$, which are identical or different, comprise linear or branched $C_1$-$C_6$ alkyl, hydroxyalkyl, or aminoalkyl groups,
  m is an integer ranging from 0 to 10;
  n is an integer ranging from 1 to 6;
  Z represents a —C(O)O— group, a —C(O)NH— group, or an oxygen atom;
  A represents a group $(CH_2)_p$, p being an integer ranging from 1 to 6;
  B represents a linear or branched $C_2$-$C_{12}$ polymethylene chain, optionally interrupted with one or more hetero atoms or hetero groups, and optionally substituted with one or more hydroxyl or amino groups; and
  $X^-$, which are identical or different, represent counterions;
 units (a) derivable from the polymerization of at least one hydrophilic monomer (a) bearing a function of acidic nature that is copolymerizable with (c);
 optionally units (n) derivable from at least one ethylenically unsaturated monomer (n) of neutral charge, which is copolymerizable with (c) and (a), wherein (n) optionally comprises an ethylenically unsaturated hydrophilic monomer compound of neutral charge bearing one or more hydrophilic groups, which is copolymerizable with (c) and (a);
 the amount of units (a) and optionally (n) range from 50% to 99.9% by number;
 the pH of the composition ranges from 5.5 to 7.5;
 the weight proportion of surfactant in the composition ranges from 0 to 30% by weight, the surfactant comprising an anionic surfactant and optionally an amphoteric surfactant; and
 the weight proportion of the copolymer in the composition ranges from 0.01% to 5%.

2. The process of claim 1, wherein the cosmetically acceptable vector is water.

3. The process of claim 1, wherein said composition comprises a shower gel comprising a surfactant in an amount ranging from 5% to 15%, or a conditioner comprising less than 5% of surfactant.

4. The process of claim 1, wherein:
 the units (c) are derived from a monomer (c) of the following formula:

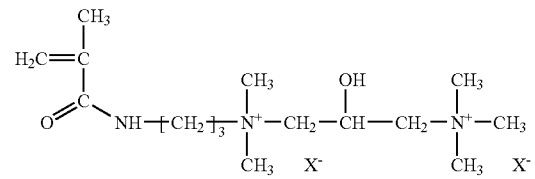

wherein:
  $X^-$ represents a chloride or methyl sulfate ion,
  the units (a) are derived from acrylic acid,
  the polymer does not comprise any units (n), and
  a numerical ratio of the units (a) to the units (c) ranges from 50/50 to 90/10.

5. The process of claim 1, wherein the surfactant is an anionic surfactant comprising an ester sulfonate, alkylbenzenesulfonate, alkyl sulfate, alkyl ether sulfate, alkylamide sulfate, alkylamidoether sulfate, fatty acid, N-acyl-N-alkyltaurate, alkylisethionate, alkyl succinamate, alkylsulfosuccinate, sulfosuccinate monoester, sulfosuccinate diester, N-acyl sarcosinate, polyethoxycarboxylate or phosphate monoester, polyethoxycarboxylate or phosphate diester, or a salt thereof, alone or as a mixture.

6. The process of claim 1, wherein the surfactant is an amphoteric surfactant comprising betaines, sulfobetaines, alkylamphoacetates, alkylamphopropionates, alkylamphohydroxypropyl sultaines, or mixtures thereof.

7. The process of claim 5, comprising:
 12% to 16% by weight of sodium alkyl ether sulfate or of a mixture of sodium alkyl ether sulfate and sodium alkyl sulfate,
 1% to 3% of an amphoteric surfactant, and
 0.5% to 2% of sodium or ammonium chloride.

8. The process of claim 6, comprising:
12% to 16% by weight of ammonium alkyl ether sulfate or of a mixture of ammonium alkyl ether sulfate and of ammonium alkyl sulfate,
1% to 3% of an amphoteric surfactant, and
0 to 2% of sodium or ammonium chloride.

9. The process of claim 5, comprising:
6% to 10% by weight of sodium alkyl ether sulfate or of a mixture of sodium alkyl ether sulfate and of sodium alkyl sulfate,
1% to 3% of an amphoteric surfactant and
2% to 4% of sodium or ammonium chloride.

10. The process of claim 1, wherein said composition further comprises a polyorganosiloxane.

11. The process of claim 10, wherein the polyorganosiloxane is a water-insoluble nonvolatile polyorganosiloxane.

12. The process of claim 11, wherein the polyorganosiloxane has a viscosity ranging from 1000 to 2 000 000 mPa.s.

13. The process of claim 11, wherein the polyorganosiloxane comprises:
a polydimethylorganosiloxanesiloxane, or
a polyorganosiloxane comprising amine, quaternary ammonium, hydroxyl, or polyoxyalkylene groups, or several of said groups.

14. The process of claim 11, wherein said composition further comprises a stabilizer and/or conditioning aid other than the polyorganosiloxane, and optionally a crosslinked polyacrylate or an insoluble solid forming a network in the composition.

15. The process of claim 11, wherein the ampholytic copolymer is transparent.

16. The process of claim 11, wherein said composition is a shampoo, a hair conditioner, a shower gel, or a composition adapted to be rinsed out.

17. The process of claim 11, wherein the polyorganosiloxane is in the form of an emulsion of droplets.

18. The process of claim 17, wherein the emulsion is an emulsion having a mean droplet size that is greater than or equal to 2 μm.

19. The process of claim 17, wherein the emulsion has a mean droplet size ranging from 0.15 μm to 2 μm.

20. The process of claim 17, wherein the emulsion has a mean droplet size that is less than or equal to 0.15 μm.

21. The process of claim 20, wherein the emulsion is a microemulsion.

22. The process of claim 17, wherein the emulsion has a mean droplet size that is greater than or equal to 0.15 μm.

23. The process of claim 17, wherein said composition comprises an emulsifier in a proportion of less than 10% by weight relative to the amount of polyorganosiloxane.

24. The process of claim 22, wherein the emulsion comprises an emulsifier in a proportion of greater than 10% by weight relative to the amount of polyorganosiloxane.

* * * * *